United States Patent [19]

Funk et al.

[11] Patent Number: 5,038,040

[45] Date of Patent: Aug. 6, 1991

[54] SOIL TEST APPARATUS

[75] Inventors: Robert C. Funk, Auburn, Ill.; Kenneth A. Sudduth, Columbia, Mo.; John W. Hummel, Urbana, Ill.

[73] Assignee: AGMED Inc., Springfield, Ill.

[21] Appl. No.: 411,055

[22] Filed: Sep. 22, 1989

[51] Int. Cl.⁵ .............................................. G01J 3/42
[52] U.S. Cl. .................................... 250/341; 250/339
[58] Field of Search .................... 250/341, 373, 339; 356/72, 445, 446, 447, 448, 402

[56] References Cited

U.S. PATENT DOCUMENTS

| Re. 31,023 | 9/1982 | Hall | 364/172 |
|---|---|---|---|
| 3,776,642 | 12/1973 | Anson | 356/188 |
| 3,828,173 | 8/1974 | Knepler | 235/151.35 |
| 3,861,788 | 1/1975 | Webster | 350/315 |
| 4,253,766 | 3/1981 | Funk | 356/418 |
| 4,266,878 | 5/1981 | Auer | 356/419 |

OTHER PUBLICATIONS

McClure, W. F., "Near IR Instru.", in: Near IR Tech. in Agricultural and Food Industries, (1987) AACC.
Williams, P. C., "Commercial Near IR Reflect Analy.", in: Near IR Tech. in Agricultural & Food Industries, (1987) AACC.
Worner, C. R., "Design & Constru. of a Portable Spectroph. for Real Time Analy. of Soil Refect. Properties", M. S. Thesis U. of Illinois at Urbana—Champaign (1989).
Sudduth & Hummel, Optimal Signal Processing for Soil Organic Matter Determination, ASAE, Jun. 26,29, 1988.

Primary Examiner—Jack I. Berman
Assistant Examiner—Richard Hanig
Attorney, Agent, or Firm—Richard Bushnell

[57] ABSTRACT

A soil test apparatus for field use comprises structure adapting the apparatus for transport over a field for testing the soil thereof; an infrared radiation generator for producing infrared radiation at a plurality of predetermined wavelengths, an elongate light carrying member coupled to the infrared radiation generator and extending therefrom for directing infrared radiation onto the soil; and a light detector for detecting infrared radiation reflected from the soil and for producing corresponding electrical signals.

36 Claims, 7 Drawing Sheets

* Hardware Triggered

SOIL TEST APPARATUS

BACKGROUND OF THE INVENTION

This invention is directed generally to the field of near infrared reflectance analysis and more particularly to a novel and improved near infrared reflectance sensing system for determining soil constituents, for example, for use in agriculture or the like.

Analysis of soil constituents is of particular interest to agriculture for optimizing conditions for the raising of various crops. Heretofore such analysis was done by taking numerous soil samples from an area to be tested and subjecting the same to painstaking and time-consuming laboratory analysis.

We have proposed to greatly simplify this process by the use of a near infrared (NIR) reflectance sensing system suitable for use in the field. It has previously been proposed to use such sensing systems for other types of analysis; for example, for analysis of grain constituents or the constituent contents of other bulk materials. However, in developing a system for determining soil constituents for in-the-field use, a number of other problems and factors arise which need to be addressed.

Among soil properties of interest are soil moisture content and cation exchange capacity (CEC). However, perhaps of primary interest is the analysis of the organic carbon content of the soil. Accordingly, our sensing system is designed particularly with the analysis of organic carbon content in mind, although it might readily be adapted to analysis of such other properties as moisture content and CEC without departing from the invention. Among problems to be addressed in the design of the system were such matters as selection of design alternatives of the sample presentation mechanism, the design of the sensor and data acquisition systems and the processing and analysis of the data acquired.

The primary considerations in selection of a sample presentation mechanism were control of the moisture content and surface roughness characteristics of the sample. Control of the sample moisture content was found to be possible by sensing below the soil surface, where less variability in soil moisture would be encountered than at the surface. Control of the surface roughness characteristics of the sample was necessary, and we found this could be accomplished by a pressing, rolling, slicing, or other mechanical action. These mechanical actions would be more easily accomplished below the soil surface, where we noted a more consistently friable soil would be found. Subsurface sensing would also avoid any irregularities in sample characteristics due to the puddling or crusting which might occur on the soil surface.

Once the need to sense a subsurface soil sample was identified, three alternative means of in situ and remote sensing were investigated:

Option 1 Transport of the soil sample to a remote sensing location while maintaining the sample structure (for example, as in a soil core).

Option 2 Transport of a fractured soil sample to a remote sensing location by an auger or similar device, followed by reconsolidation of the sample for measurement.

Option 3 In situ sensing of a surface prepared by some type of furrow opener. Option 2, transport of a fractured soil sample, was eliminated from consideration due to several disadvantages. This system would have an inherent lag time, severely limiting operating speed. The process of soil detachment, transport, and repacking could introduce bias due to size and/or density sorting of the soil particles. However, option 2 did have several advantages: intermittent sampling with a sample device would be possible; the sensor optical path could be made compact; and a reflectance standard could be incorporated into the mechanism.

Option 1, transport of a consolidated soil sample, was considered in more detail. This concept used an automated device to extract a soil core and to position the core for scanning through a window in the side of the soil coring tube. A pneumatically driven core sampler was fabricated to test the soil coring concept in the laboratory. The sampler used a 150 mm stroke double-acting cylinder controlled by a four-way solenoid actuated valve connected to a 1 MPa building air supply. A 12 V time delay relay provided the control input to the solenoid, porting air to the head of the cylinder for an adjustable time interval when an input signal was applied. The relay was set such that the sampler experienced a minimum dwell time at the fully extended position and then began its return stroke, with a total cycle time of 0.4 sec. A spring-loaded pivoting break-away action was provided between the coring unit and a carrier subplate so that the corer could maintain position during the coring operation, while the carrier was moving with a horizontal velocity.

Three interchangeable soil coring tubes could be attached to the cylinder rod. These tubes provided a range of cutting and core compaction alternatives for use in varying soil conditions. Two of the tubes were standard equipment for a JMC soil sampler (Clements Associates, Inc., Newton, Iowa). The JMC "wet" sampling tube, intended for use in wetter or more cohesive soil conditions, had a long tapered cutting bit and considerable relief from the bit diameter (17 mm) to the tube diameter. The JMC "dry" tube bit was shorter and larger in diameter (19 mm) with less relief. These two tubes were fitted with an external sleeve which contained the soil core while providing a window through which the sensor could operate. The third coring tube was fabricated from 25 mm diameter steel tubing by chamfering the lower edge to create a cutting bit. No relief was provided between the bit area and the remainder of the tube.

Initial stationary tests of the coring unit were accomplished with recompacted, moist samples of Drummer Silty Clay Loam obtained at the University of Illinois Agricultural Engineering farm. No difference in core quality was observed between the two JMC bits, with both collecting acceptable samples. The straight coring tube did not obtain a satisfactory core in these conditions, due to excessive adhesion of the soil to the inner diameter of the tube.

Additional soil coring unit tests were carried out in the soil bin at the Deere and Company Technical Center, Moline, Ill. The soil used was a mixture of 40% fine river sand and 60% clay, with a moisture content of 8.5 percent. Stationary and moving tests were completed at three cone index levels, 0.5 MPa, 0.75 MPa, and 1.0 MPa. The speed limit for forming an acceptable soil core with the coring unit as tested was approximately 0.25 m/s. However, it appeared that a more refined method of holding the coring unit stationary relative to the soil surface while sampling could increase the speed operating range. Only the straight bore tube produced acceptable cores in the soil bin tests, and then only with marginal reliability. Small differences in soil moisture or cone index level resulted, on occasion, in incomplete cores being obtained. Cores collected in this high sand content, low cohesion soil with the JMC tubes fell apart easily.

Based upon the difficulties in obtaining a complete soil core reliably across a range of soil types and physical conditions, the core sampler method of sample presentation was eliminated from further consideration.

Because of the problems encountered with the remote sample presentation methods described above, it was decided to pursue in situ sensing. This method had disadvantages in difficulty of reflectance calibration and inability to hold the sample stationary while data were being acquired, but it seemed to hold the best promise for development of a workable prototype field sensor.

OBJECTS AND SUMMARY OF THE INVENTION

Accordingly, it is a general object of this invention to provide a novel and improved soil analysis apparatus for field use.

Briefly, and in accordance with the foregoing object and other considerations, a soil test apparatus for field use in accordance with the invention comprises means for adapting said apparatus for transport over a field for testing the soil thereof; infrared radiation generating means for producing infrared radiation at a plurality of predetermined wavelengths; light carrying means coupled to said infrared radiation generating means and extending therefrom for directing infrared radiation onto the soil; and light detecting means for detecting infrared radiation reflected from the soil and for producing corresponding electrical signals.

BRIEF DESCRIPTION OF THE DRAWINGS

The features of the present invention which are believed to be novel are set forth with particularity in the appended claims. The organization and manner of the operation of the invention, together with the further objects and advantages thereof may best be understood by reference to the following description, taken in connection with the accompanying drawing in which like reference numerals identify like elements, and in which:

DETAILED DESCRIPTION OF THE ILLUSTRATED EMBODIMENT

Figure 1:
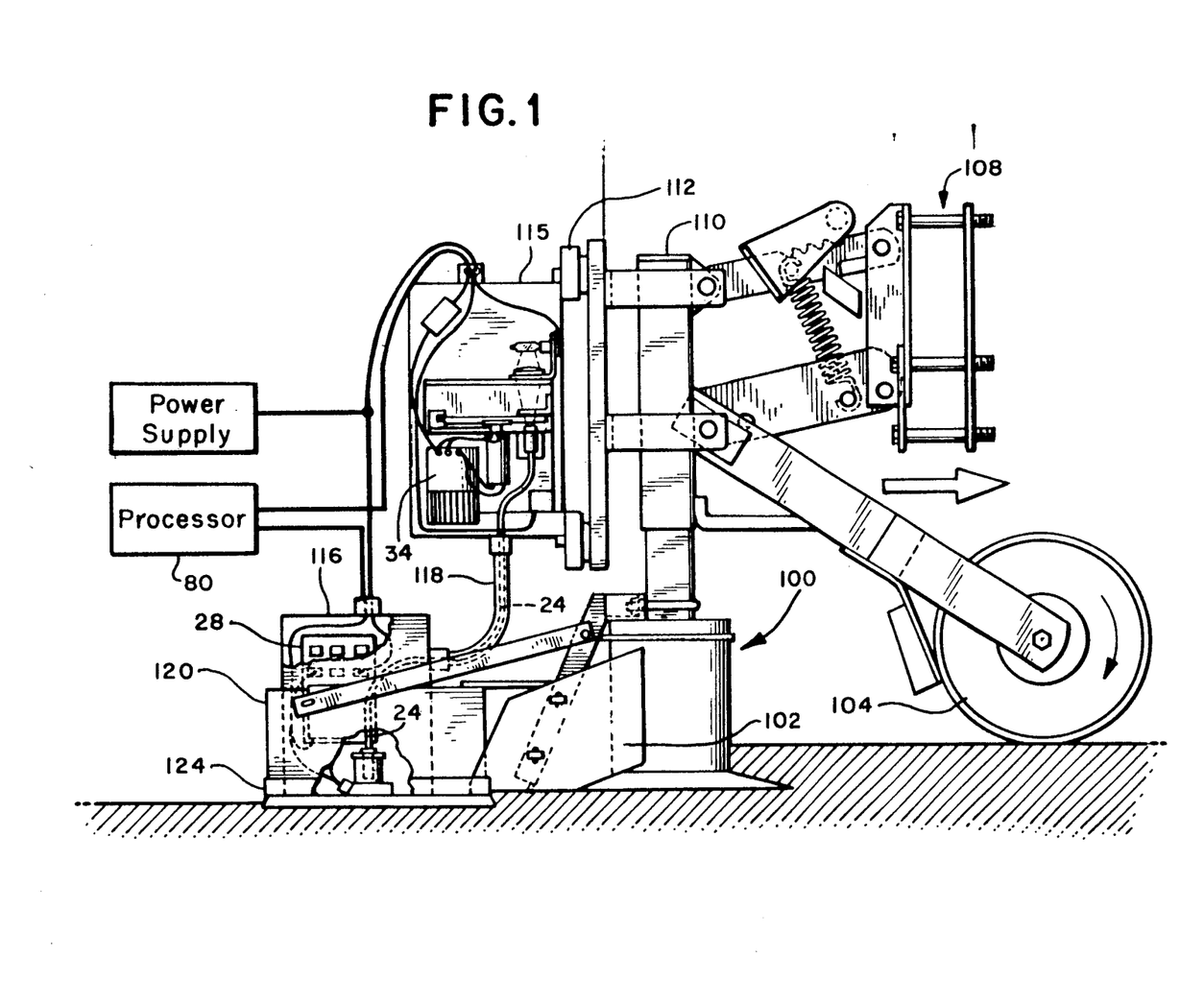
FIG. 1 is a side elevation, partially broken away and somewhat diagrammatic in form, of a soil analysis test apparatus in accordance with the invention.

Referring now to the drawings, and initially to FIG. 1, a near infrared (NIR) reflectance sensing system is designed, fabricated, and evaluated for field use in testing soil. The overall design objective for this soil test apparatus (e.g., for predicting organic matter content of soil in the field) is to implement a prediction method on a near real-time basis. Specific design objectives for the sensor system are:

1) a bandpass of 60 nm or less over a minimum sensing range from 1700 to 2420 nm, to implement the previously selected sensing method;

2) an essentially continuous (in wavelength) sensing method, to allow flexibility for additional optimization of the wavelengths selected for the prediction algorithm;

3) Potential, with additional refinements if needed, to acquire enough information to make a control decision every 4.5 seconds (This rate corresponds to a 10 m (40 ft) spacing at a 2.2 m/s (5 mi/h) travel speed);

4) ability to predict soil organic matter content with a standard error of prediction less than 0.5 percent (or less than 0.29 percent organic carbon) for the 30 Illinois soils in an initial, preselected calibration dataset;

5) Tolerance of dust, temperature fluctuations, shock loads, and vibration, such as would be encountered if the sensor were operated in the field.

The initial choice in the design process is between purchase of a commercial NIR instrument and design and fabrication of a new sensing system tailored to meet the specific requirements outlined above. The commercially available NIR instruments generally fall into two categories (Williams, 1987a). The grating monochromator and tilting filter instruments measure reflectance at more wavelengths than required and at a narrower bandwidth, and this excess capability results in high costs. Additionally, these instruments are not designed for the environmental stresses imposed by use in a field environment, and would be limited to laboratory use. Fixed filter instruments are more rugged and less expensive, but obtain reflectance measurements at fewer wavelengths than required by the organic matter prediction algorithm. Since no commercially available NIR instrument met all the design objectives, it was decided to develop a prototype sensor specifically targeted at NIR reflectance sensing of soil organic matter content.

Once the decision was made to design a dedicated instrument, the wavelength selection mechanism and detector were chosen. These are the major components of the optical system, and as such dictate much of the configuration of the remainder of the system.

A review of available NIR photoelectric detectors led to the choice of a lead sulfide (PbS) unit for this design. The PbS detector has advantages over the other available types (notably PbSe and InAs) in the areas of cost, responsivity, and ability to operate without cooling. The next decision in detector selection is the choice of a single element detector or an array detector. A single element detector would be used with a wavelength selection mechanism (in this case, a monochromator) which scans the wavelengths of interest sequentially onto the detector. An array detector could be used if the wavelength selection mechanism (in this case properly termed a spectrograph, but usually called a monochromator) focuses the wavelengths of interest into a line image on a flat focal plane, thus providing simultaneous sensing at all wavelengths.

Three design alternatives were considered for the wavelength selection mechanism; a grating monochromator, a prism, and a circular variable interference filter. The grating monochromator is the usual device used in NIR laboratory spectrophotometers (McClure, 1987), but environmental considerations such as dust and vibration sensitivity make its use more difficult for a field instrument. Worner (1989) constructs a visible spectrophotometer using a prism and a linear array detector in an attempt to overcome the environmental problems seen with gratings. Circular variable filters have been used in rugged field instruments for portable color measurement (Jauch, 1979) and for airborne infrared spectral measurements (Hovis et al, 1967).

Using the above detector and monochromator alternatives, five possible combinations are identified:
1. Grating and single detector
2. Grating and array detector
3. Prism and single detector
4. Prism and array detector
5. Circular variable filter and single detector Option 1, a grating monochromator with a single detector, requires oscillation of the grating to scan all wavelengths of interest onto the detector. The mechanical freedom required for this movement would also make the device prone to vibration-induced inaccuracies. Another possible problem with a grating instrument was dust contamination; even a small amount of dust on the surface of a grating would render it useless, thus requiring its replacement. However, it was felt that the monochromator could be sealed well enough that this sensitivity to dust would not be a major problem in field use.

Options 3 and 4 use a prism monochromator, however, none was available as a stock item in the wavelength range required. The costs and lead time associated with custom prism design and fabrication were not desirable within the scope of this project. Use of the prism with a single detector requires a scanning mechanism and would entail the same type of vibration problems seen in the grating system. The nonlinear dispersion characteristics of a prism make it difficult to provide data at equal wavelength spacings with an array detector. Due to these problems and the fact that the prism monochromator does not have any distinct advantages over the grating monochromator if the latter could be sealed against dust, the prism monochromator options were dropped from consideration.

Primary consideration, then, was between option 2, grating monochromator and array detector, and option 5, circular variable filter monochromator and single element detector. A detailed vendor survey was completed to identify the optimal stock components usable in these two alternatives. After consideration of the components thus identified, the combination of circular variable filter monochromator and single element detector was selected. The primary reason for this selection was the greater flexibility offered by the circular variable filter (CVF) approach.

A CVF was available with a wavelength range of 1600 to 2900 nm and a bandwidth of approximately 55 nm (Optical Coating Laboratory, Inc., Santa Rosa, Calif.). This provides extra capability on either end of the required sensing range (1700 to 2420 nm) while meeting the 60 nm bandwidth requirement. Additional flexibility is realized with the CVF since reflectance readings can be taken at any desired point in the wavelength range, subject only to the limitations of the data acquisition system. In contrast, the best combination of grating monochromator and linear array detector did not completely cover the required range and allowed sensing only from 1720 to 2380 nm. This combination had a theoretical bandwidth of 36 nm, but could output only 16 reflectance readings, corresponding to the 16 elements of the linear array. Other factors favoring the choice of the CVF system are its greater tolerance of dust and vibration, and a reduced degree of complexity in the interface electronics (due to the use of one data channel versus 16). A possible drawback of the CVF system is that it would not acquire data at all wavelengths simultaneously, but rather in sequence. It is possible that sequential wavelength scanning might require holding the soil sample stationary while data are being acquired, so that all wavelengths are scanned on an identical area of the sample.

It should be understood that all of the design alternatives mentioned herein are to be considered as falling within the scope of the invention. The particular design choices and the embodiments more particularly described hereinafter are for purposes of description, and should not be construed as limiting the invention in any way.

Figures 2, 3:
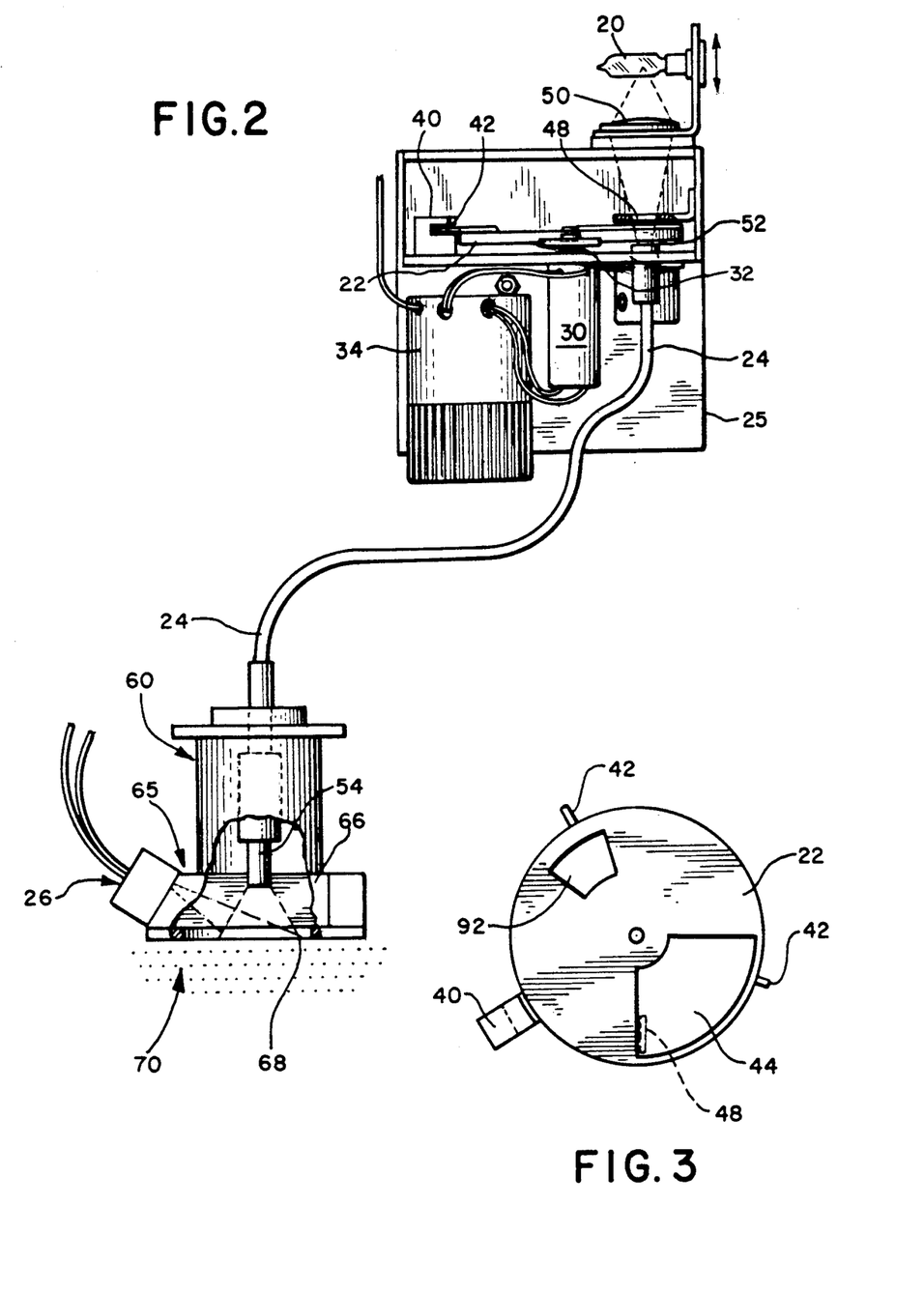
FIG. 2 is an enlarged, broken away and somewhat diagrammatic view of a sensor assembly or portion of the apparatus of FIG. 1.
FIG. 3 is a top plan view of a circular variable filter segment with related timing components in accordance with a preferred embodiment of the apparatus of FIG. 1.

An overall schematic of the NIR soil organic matter sensor is shown in FIGS. 1, 2 and 3. The optical path of the sensor includes a broadband NIR source 20, a quarter-segment circular variable filter (CVF) monochromator 22, a fiber optic bundle 24 before the sample, and a lead sulfide detector 26 to measure the reflected energy. Output of the detector 26 is conditioned by a pre-amplifier 28 and input to processing means 80 comprising a personal computer or other suitable processor and an analog-to-digital (A/D) converter through which the data enters the processor.

A housing 25 forms the main mounting structure for this part of the instrument. Instead of using a separate chopper disk, modulation of the lamp output radiation for low frequency noise and drift rejection is accomplished with the filter disk 22 itself. By spinning the filter disk at a sufficient rate and using the three-quarters of the filter disk which blocks the light path to perform the modulation function, the need for a separate motor, chopping disk, and sensing electronics is avoided.

To allow adjustment of the filter disk rotation speed, a servo-controlled motor-generator 30 is used (Motomatic E-350, Robbins & Meyers, Hopkins, Minn.). The permanent magnet DC motor-generator set 30 is mounted under the filter 22 and the filter disk 22 is attached directly to the motor-generator shaft 32. A solid-state electronic controller and speed setpoint potentiometer 34 are attached to the rear of the filter housing 25. The system is powered through a transformer by 115 VAC. Although the maximum speed of the motor-generator set is much higher, the design operation speed in this application is 10 Hz (600 rpm) or less, due to balancing considerations in the filter disk assembly.

A 50 W, 12 V quartz halogen automotive-type lamp driven by a laboratory power supply is used as the illumination source 20 for the sensor. The lamp mounting allowed three-axis adjustment for focusing and positioning the lamp image. A spherical biconvex lens 50 is mounted in the upper surface of the filter housing to focus the lamp image through the input slit 48 and onto the surface of the CVF 22. The wavelength of the light which passes through the CVF at any point on the filter is a linear function of the angular position of that point relative to the leading edge of the filter. Therefore to obtain monochromatic (or nearly monochromatic) light from the system, a plate or shield 46 with a narrow radial slit 48 (2 mm wide by 10 mm radial length) is mounted about 5 mm above the surface of the filter. Since the projected image of the lamp filament is of a similar size and shape, only a small portion of the lamp energy is blocked at the slit.

Figure 4:
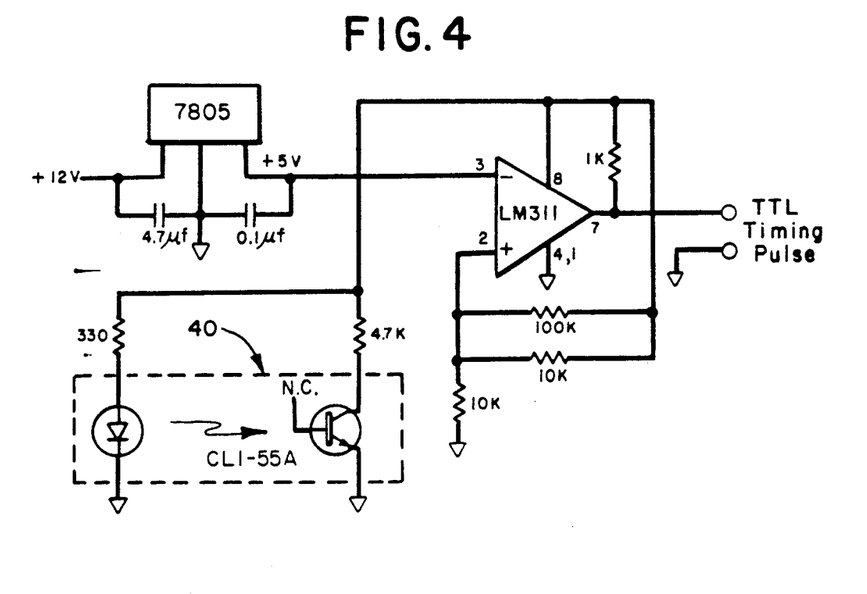
FIG. 4 is a schematic diagram of a circuit useful with the timing arrangement of FIG. 3.

An opto-interrupter 40 is mounted within the filter housing such that its optical path is broken once per filter disk revolution by a small tab 42 attached to the circumference of the disk 22. The timing pulse generated by the opto-interrupter is conditioned to TTL levels by a Schmitt trigger circuit (FIG. 4). This TTL signal is then used to compensate for any variations in the speed of revolution of the filter disk and to provide a positive angular position reference for wavelength determination.

Two positions for the timing tab were used for the laboratory tests. The tab position used initially was opposite the CVF segment 44 on the filter disk 22. Later, the tab was placed adjacent to the CVF segment on the filter disk. The tab was moved so that its timing pulse would coincide more closely with the analog reflectance signal which was generated by the photodetector 26 when the CVF was aligned with the slit 48.

The monochromatic light from the CVF is directed to the soil surface by means of a 610 mm long silica fiber optic bundle 24 with a useful transmission range of 350 nm to over 2400 nm, obtained from Volpi Fiber Optics, Auburn, N.Y. The bundle is termed a section converter, as the fiber area changes shape from a 1 mm by 10 mm rectangular section at one end 52 to a 3.6 mm circular cross-section at the other end 54. The rectangular section end 52 of the fiber bundle 24 is mounted approximately 5 mm below the surface of the CVR 22 and in line with the input slit 48, thus collecting the majority of the filter output energy. The fiber 24 then exits the bottom of the filter housing and is routed to a light-tight sample chamber 60. Within the sample chamber, the circular cross-section end of the fiber optic bundle is mounted to a sensor head assembly 65. This mounting is adjustable, allowing optimization of the location of the fiber exit cone with respect to the detector and the soil surface.

The sensor head assembly 65 consists of an aluminum housing 66 with a quartz aperture on window 68, and the PbS detector attached thereto. Input monochromatic light from the fiber optic bundle 24 passes through the quartz aperture window 68 and illuminates a circular area on the sample surface 70. A portion of the energy is diffusely reflected from the sample and passed back through the quartz aperture and collected by the OTC-22-53 PbS photodetector 26 (OptoElectronics, Petaluma, Calif.). This detector has a useful sensing range from 1000 to 3500 nm, a 3 mm by 3 mm square sensing area, and could be thermoelectrically cooled for increased sensitivity.

Excitation and preamplifier circuitry (FIG. 5) for the PbS detector includes a high-gain single stage amplifier AC coupled to the output of the detector, which is insensitive to low frequency drift in the detector output. A DC power supply (not shown) provides ±15 V DC to this circuit.

The processing means 80, indicated diagrammatically, is a MetraByte DAS-16 analog and digital input-output (I/O) expansion board installed in an AT-compatible computer (such as a Texas Instruments Business Pro) running at 12 MHz. Features available on the DAS-16 board include 16 single end or 8 differential analog input channels scanned by a 12 fit successive approximation analog-to-digital (A/D) converter, a three-channel programmable interval timer, two channels of 12 bit digital-to-analog output, one 4 bit digital input port, and one 4 bit digital output port. The software is provided with the DAS-16 includes a machine language driver which controls I/O operations by calls from interpreted or compiled BASIC. Drivers are available in other programming languages and the user could develop customized I/O control routines in assembly language if desired. The manufacturer's stated maximum sampling rate for the DAS-16 is 60 Khz, which can be achieved by direct memory access (DMA) transfer of the digitized input data to computer memory. Interrupt driven transfers or direct data transfers to a BASIC array allows the A/D system to attain sampling rates of up to 3 KHz, according to the manufacturer.

Figure 5:
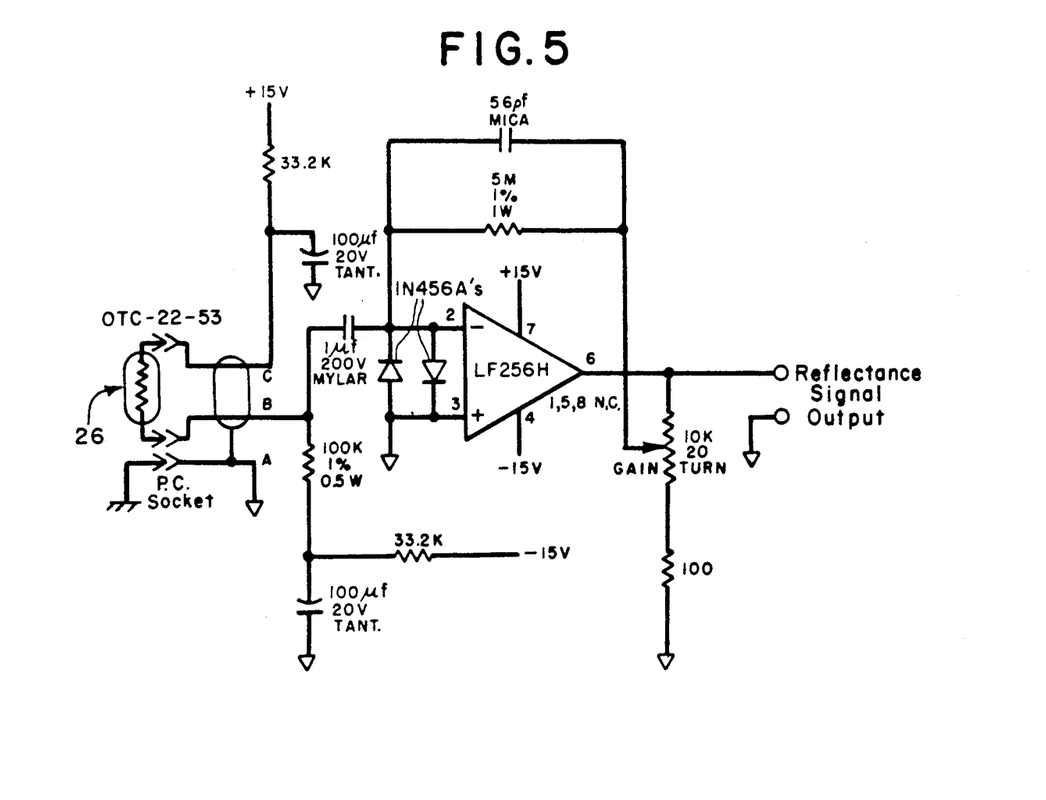
FIG. 5 is a schematic circuit diagram of a reflectance signal input circuit in accordance with a preferred embodiment illustrated herein.

Data collection from the soil organic matter sensor requires use of both analog and digital inputs on the DAS-16. One differential analog channel, configured with a ±5 V range, is used to collect data from the photodetector preamplifier (FIG. 5). The TTL output from the filter disk timing circuit (FIG. 4) is input as a digital signal so that the time during which its level is high during each disk revolution can be determined by counting gated timer pulses. The timing tab signal is also used to gate the A/D converter and synchronize date collection.

Figure 6:
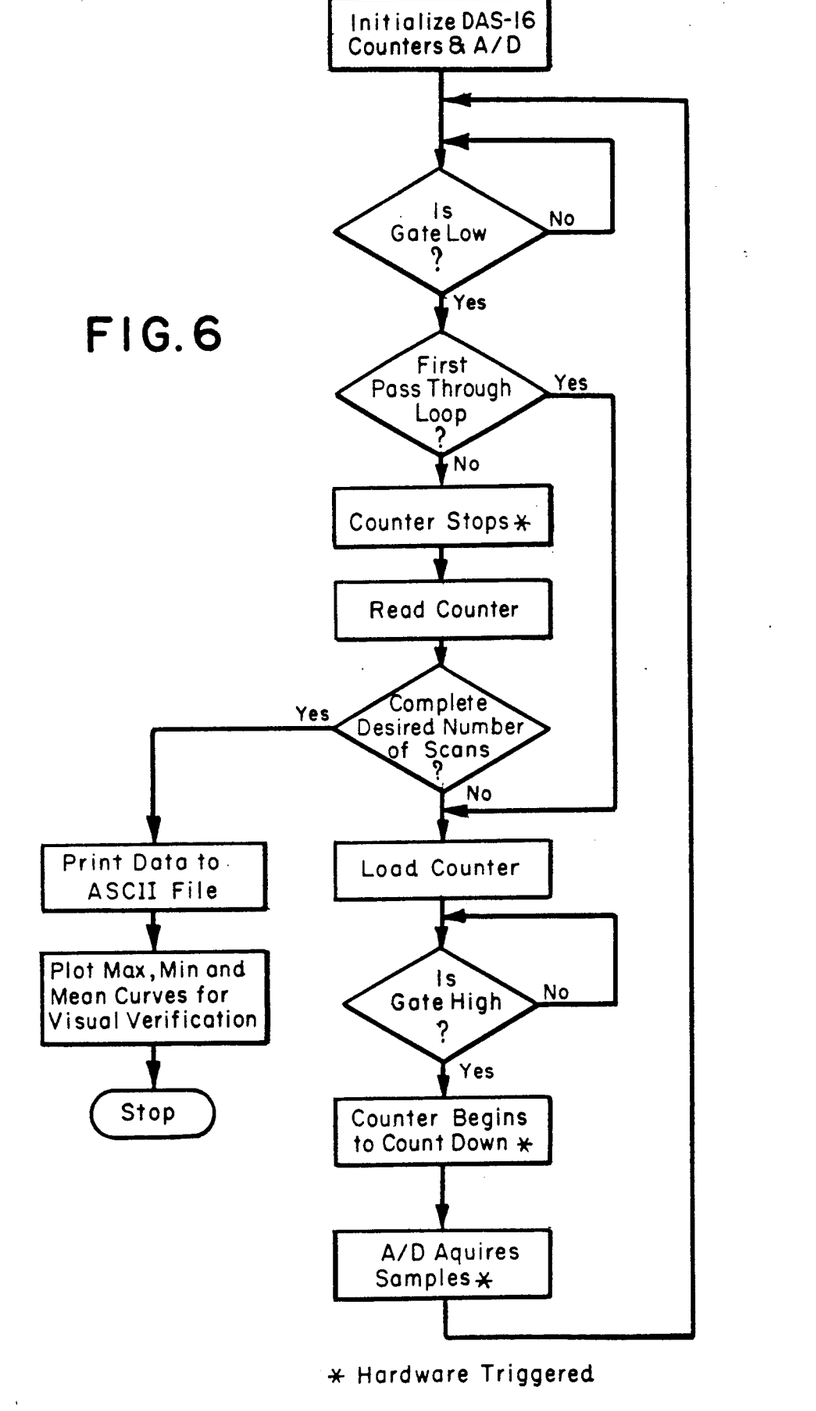
FIG. 6 is a flow chart illustrating a data acquisition and analysis process useful with the apparatus of the invention.

The required A/D sampling rate is approximately 10 KHz, based upon the geometry of the CVF 22, a 10 Hz (600 rpm) maximum frequency of revolution for the filter disk, and a desire to obtain the reflectance data on a 5 nm maximum spacing. With this high sampling rate it was decided to transfer the A/D data directly to an array, using a program written in IBM compiled BASIC (see FIG. 6). This program allows analog data acquisition simultaneously with counter operation to time the width of the gate created by the rotation of the filter disk. The data from up to ten consecutive revolutions of the filter disk can be acquired, stored on disk for later analysis, and displayed for visual verification.

Figure 7:
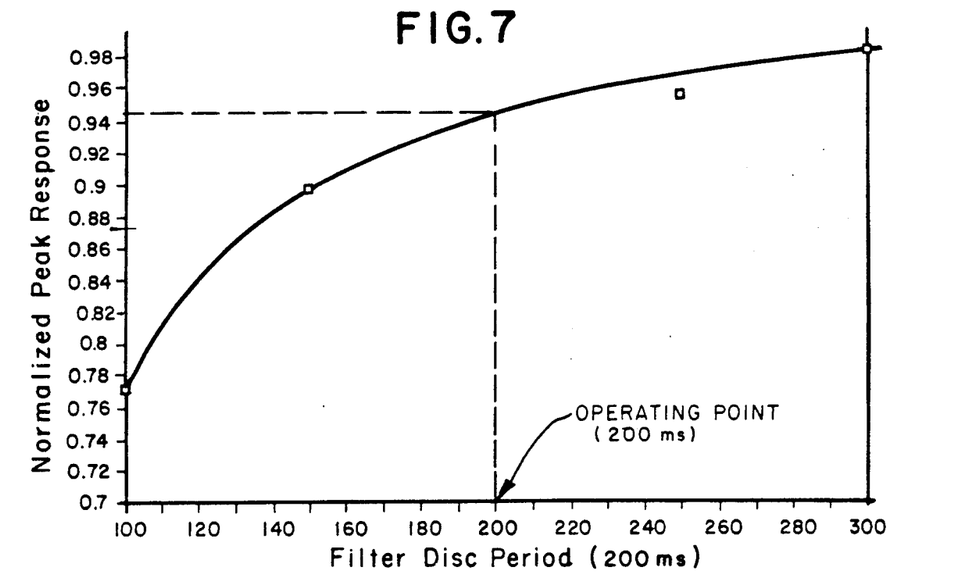
FIG. 7 is a graphical representation of a normalized peak response curve obtained with the apparatus of the invention.

To test the response of the detector, a window 92 (see FIG. 3) was placed in the filter disk directly opposite the CVF segment. This was for test purposes only and forms no part of the invention. During normal operation this window is completely occluded, but for detector response tests a special shutter with two openings was installed. The first opening allows measurement of the pulse response of the detector while simulating a pulse caused by the interaction of the slit and a point of interest on the CVF, while the second, wider opening allows the final step response of the detector to be quantified. The data acquisition system is used in this response test to record the detector output from a ceramic standard reflecting surface at filter disk periods from 100 ms to 300 ms. To avoid saturating the detector, the lamp voltage is set at 5.0 V and three layers of lens tissue placed between the lamp and the focusing lens. The relationship between the 1 mm pulse response and filter disk period is shown in FIG. 7. As a compromise between the increasing signal level with longer disk period and the desire to collect data as quickly as possible for field operation, a filter disk period of 200 ms (speed of 5 Hz, i.e., 300 rpm) was selected for subsequent tests.

Another functional test investigates the relationship between sample distance and signal level to determine the optimum operating distance from the soil surface. Using a ceramic standard as the reflecting surface, the location of the sensing head is varied from 6.4 mm to 25.4 mm above the surface and the output signal recorded.

Figure 8:
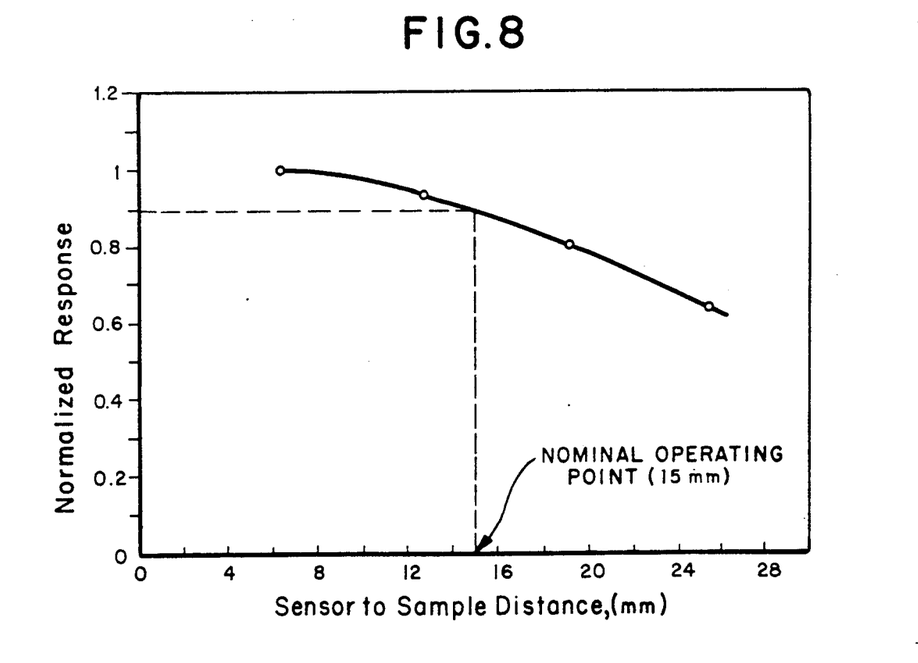
FIG. 8 is a graphical representation of the relationship between sample distance and signal level obtained with apparatus of the invention.

A curvilinear relationship was found between sample distance and signal level (FIG. 8). The decrease in the signal with increasing sample distance indicates that operation at the minimum distance is desirable. Decreasing sample distance, however, will have two detrimental effects. First, in a field unit some allowance must be made to compensate for the inability to hold distance perfectly constant. Also, decreasing the distance to the sample also decreases the area of the sample being sensed. For a nonuniform material such as soil, it is desirable to sense a sufficiently large area to average out signal differences due to any heterogeneity found within a given sample. As a compromise between signal strength and these two effects, a nominal sensor-to-sample operating distance of 15 mm was selected.

During a test designed to compensate for changes in illumination, detector response, and other optical system variations, each sensor reading is referenced to the reading from a ceramic disk, a substance widely accepted for standardization of NIR instruments. Besides providing a means to calibrate for system variations, the ceramic reference also enables conversion of the response to a percent reflectance (or decimal reflectance) basis.

Two identical ceramic disks are used in this calibration procedure. One 50 mm diameter disk, mounted in a flat black aluminum block, is used as the reflectance standard for the sensor. The other disk is sent to the USDA Instrumentation and Sensing Laboratory, where its reflectance characteristics are obtained by comparison with a standard sample of slightly compressed sulfur. A series of ten paired readings of both ceramic disks is then completed with the sensor in the laboratory. The mean of these ten readings is used to compute the decimal reflectance characteristics of the ceramic disk used for sensor calibration.

Figure 10:
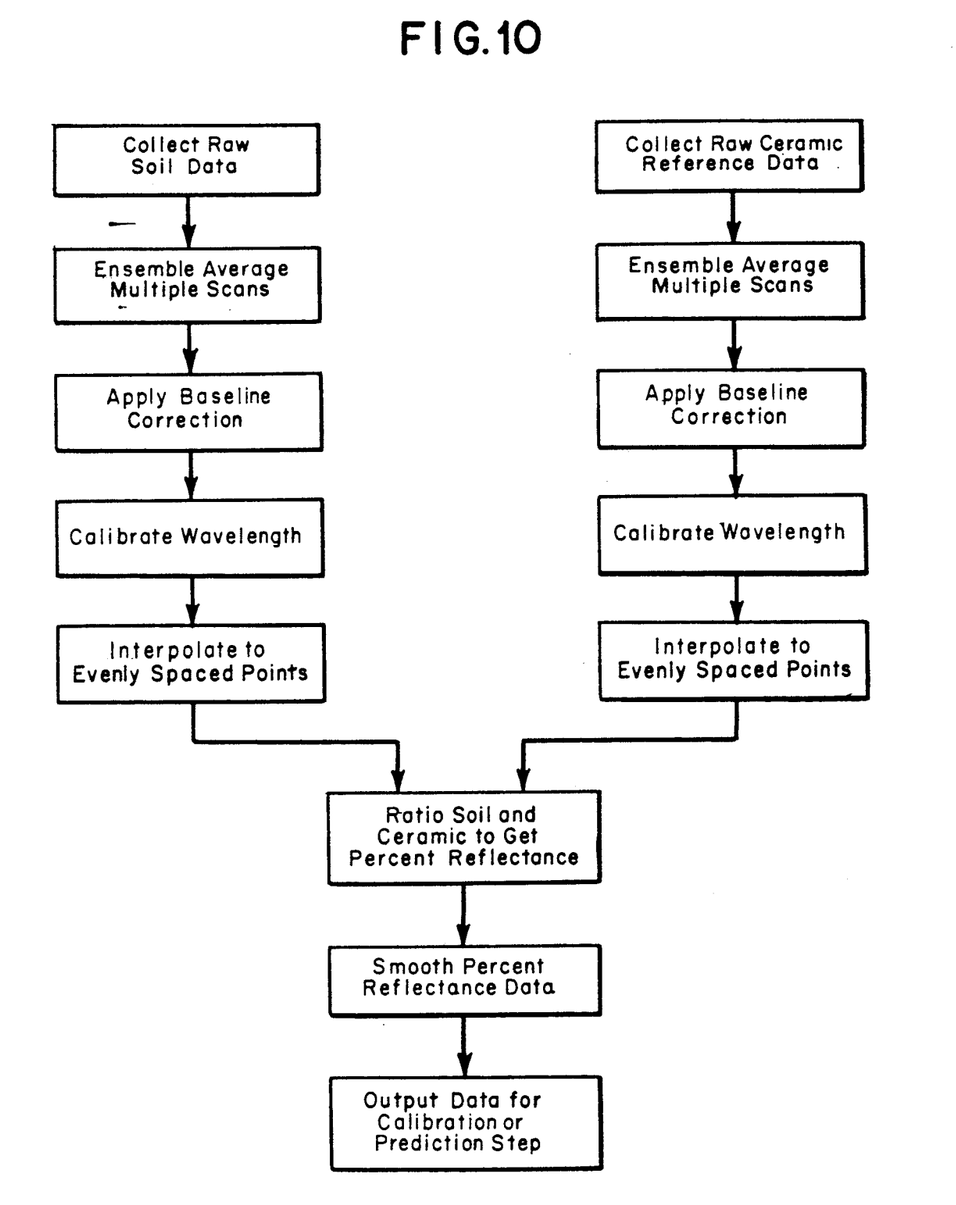
FIG. 10 is flow chart illustrating a preferred mode of operation of the apparatus of the invention.

Several data processing steps are necessary to convert the raw digitized data obtained from the sensor and stored by the data collection program to the percent reflectance data needed to calibrate the sensor and predict soil organic matter content (FIG. 10). The algorithms are implemented in three BASIC programs. CORR1.BAS reads the data files created by the data acquisition program, performs scan averaging, baseline corrections, and wavelength calibration, and writes an output file containing the corrected raw data. INTERP1.BAS reads in raw data files for a soil sample and the corresponding ceramic reference sample, interpolates these data to the same evenly spaced (in wavelength) points, ratios the two datasets to obtain a percent reflectance reading, and stores the reflectance data. MAK1.BAS reads the reflectance data files for a set of samples, smooths the data to the required point spacing, and outputs a file formatted correctly for the calibration and prediction programs.

Multiple scans of raw reflectance data taken on each sample are averaged point by point to improve the signal to noise ratio. The main analyses were completed with 10-scan averaging, but some supplementary analyses averaged other numbers of scans. Further analyses were similar in most respects; however, different reference materials and numbers of data points were used in some instances.

Figure 11:
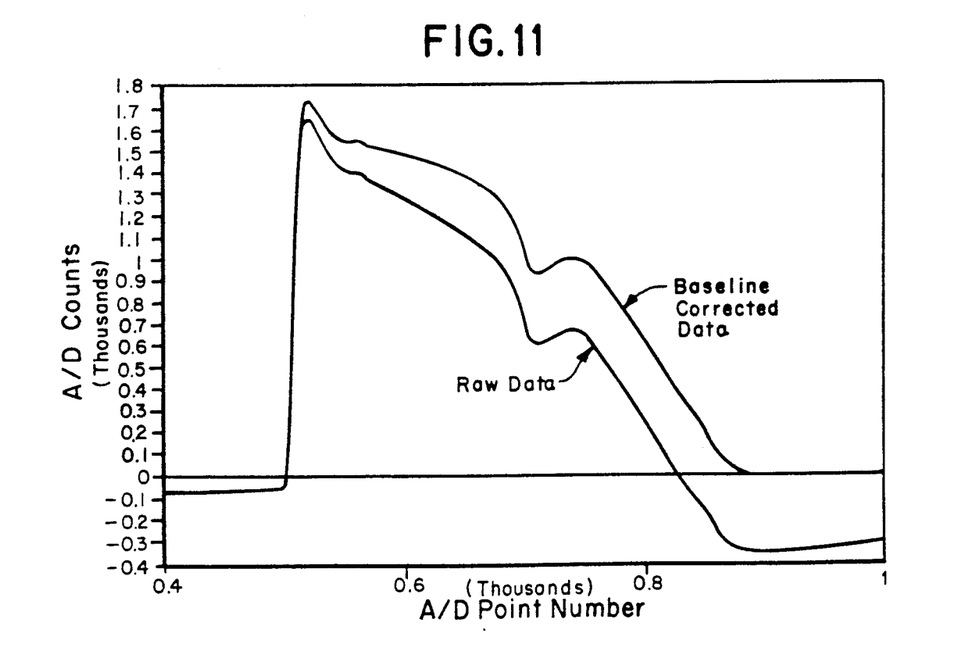
FIG. 11 is a graphical representation indicating further the process of obtaining baseline corrected data from the raw data obtained from the apparatus of the invention.

A dynamic baseline correction algorithm is used to convert the AC coupled raw reflectance signal to a DC signal with a baseline level of zero A/D counts (see FIG. 11). Referring to the schematic of the detector and preamplifier (FIG. 5), the parameter which varies directly with the level of incident radiation is the current through the photodetector, $I_{in}$. The parameter digitized by the data collection system is the output voltage of the preamplifier $V_{out}$. The general relationship between these two parameters at any point was given by:

$$i_{in} = k_1 + k_2 * V_{out} + k_3 * \int V_{out}\, dt \tag{12}$$

The output voltage, $V_{out}$ could be converted to A/D counts by application of a gain and offset:

$$D_{raw} = a_0 + a_1 * V_{out} \tag{13}$$

$$V_{out} = a_3 + a_r * D_{raw} \tag{14}$$

Equation (12) could be digitized and rewritten with the raw A/D data $D_{raw}$, replacing $V_{out}$ and the corrected A/D counts, $D_{corr}$, replacing $i_{in}$:

$$D_{corr} = c_1 + c_2 * D_{raw} + c_3 * \sum_1^n (D_{raw} + c_4) \tag{15}$$

Equation (15) could be simplified by setting $c_2$ to one, since the units of $D_{raw}$ were the same as the units of $D_{corr}$. Also, $c_4$ could be removed from under the summation.

$$D_{corr} = D_{raw} + c_1 + c_4 * n + c_3 * \sum_1^n D_{raw} \tag{16}$$

Determination of $D_{corr}$ for any given $D_{raw}$ then required the values of three parameters to be determined. These values were unique to each particular data curve, due to the differences in total reflected energy between samples. To determine $c_1$, $c_3$, and $c_4$ it was necessary to make use of the fact that $D_{corr}$ should, on the average, be zero in the baseline portions of the curve. Then, in these two portions of the data curve, Equation 16 could be rewritten as:

$$D_{raw} = -c_1 - c_4 * n - c_3 * \sum_1^n D_{raw} \tag{17}$$

Equation (17) was then fit to the data in the baseline areas of the curve using a least-squares multiple linear regression, where the independent variables at each data point were the index number of the data point and the summation of the raw A/D data up to that point. The dependent variable was the raw A/D data value. The equation was fit to a 167-point section of the baseline on either side of the data portion of the curve, corresponding to 16.67 ms at a 10 kHz sampling rate. In this way, the baseline correction was fit to the mean of any 60 Hz noise present in the data. The algorithm to the baseline correction coefficients was:

Defining:

$$X_{(n-ni),0} = 1 \tag{18}$$

$$X_{(n-ni),1} = n \tag{19}$$

$$X_{(n-ni),2} = \sum_{1}^{n} D_{raw} \tag{20}$$

$$y_{(n-ni)} = \overline{D_{raw}} \tag{21}$$

Where the range of n was from 334 to 500 (with $ni=333$) and 901 to 1067 (with $ni=733$)

Then:

$$b=(X^TX)^{-1}X^Ty \tag{22}$$

$$c_1 = -b_0 \tag{23}$$

$$c_4 = -b_1 \tag{24}$$

$$c_3 = -b_2 \tag{25}$$

With the necessary constants determined in this manner, Equation (16) is then applied pointwise to the raw A/D data to generate a baseline corrected raw data curve (FIG. 11).

Figure 9:
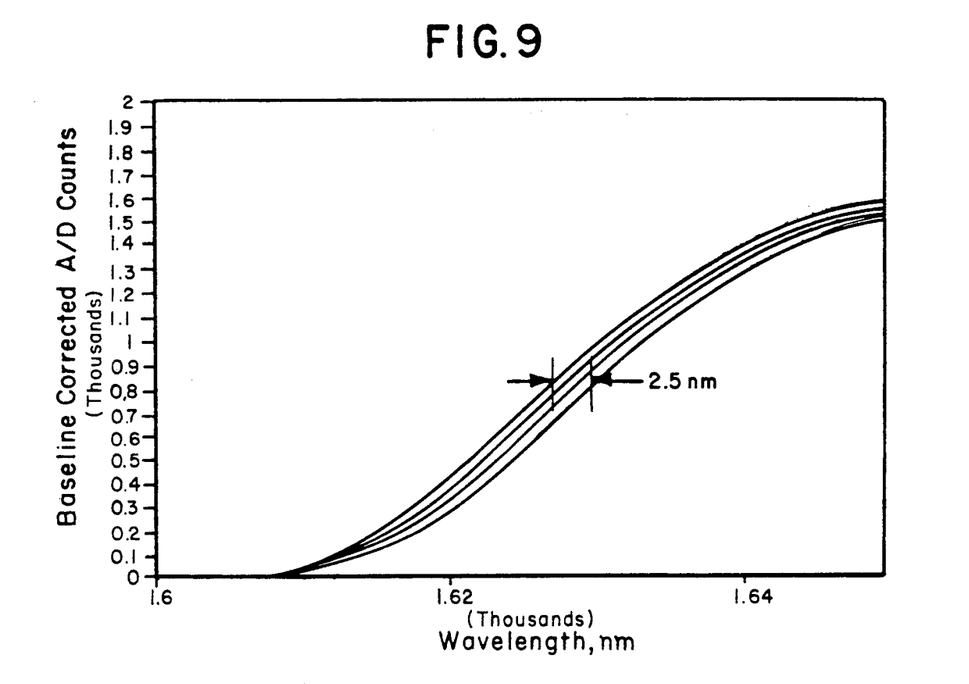
FIG. 9 is a graphical representation of deviation in the raw reflectance curve indicating a wavelength calibration in the operation of the processor portion of the apparatus of the invention.

The calibration developed by use of fixed filters is applied to the data to convert the A/D point number to its corresponding wavelength. An additional calibration is used to compensate for the remaining wavelength variation at the initial step response portion of the curve (FIG. 9). The wavelength at the half-peak point on this portion of the curve is calculated and compared to the mean value of the half-peak point obtained from a set of 225 soil and ceramic reflectance scans. This wavelength offset is then applied to each point on the curve so that the half-peak point of each individual curve is coincident with the mean half-peak point. Therefore, the initial portion of the response curve is normalized with respect to wavelength, but any sub-period speed variations could cause shifts elsewhere in the curve.

Due to wavelength calibration differences and variations in filter disk period, a given A/D point will not correspond to the same wavelength for all reflectance readings. Therefore, it is necessary to interpolate the baseline corrected sensor response data to a standard wavelength spacing for pointwise differencing of soil and ceramic readings and additional analysis. Points are generated every 5 nm from 1600 nm to 2700 nm using piecewise cubic spline interpolation algorithms presented by Spath (1974).

The interpolated, baseline corrected raw data obtained from the sensor are converted to decimal reflectance (percent reflectance/100) by comparison against data obtained from a ceramic disk with a known reflectance in the range of interest. Repeated readings of the ceramic disk are done on a frequent basis to that compensation can be made for lamp output fluctuations or other changes in the optical path of the sensor. Decimal reflectance at each point is calculated by:

$$REFL = REFL_{ceramic} * DCORR + DCORP_{ceramic} \tag{26}$$

Where:
REFL = decimal reflectance
DCORR = interpolated and baseline corrected sensor data Decimal reflectance data are transformed to optical density (OD) for calibration and subsequent analysis. Prior to this transformation, the reflectance data are smoothed from a 5 nm point spacing to a 20 nm spacing for noise reduction and compatibility with the analysis programs The operations performed on each point on the reflectance curve are:

$$\begin{aligned} RS_i = 0.125 * \\ (REFL_{i-2} + 2*REFL_{i-1} + 2*REFL_i + 2*RE\text{-} \\ FL_{i+1} + REFL_{i+2}) \end{aligned} \tag{27}$$

$$OD_i = -\log_{10} RS_i \tag{28}$$

Where:
REFL = decimal reflectance
RS = smoothed decimal reflectance
OD = optical density Cation exchange capacity (CEC) and soil moisture content are also predicted with the reflectance data. For these calibrations, 40 nm data (1640 to 2640 nm) are used, with 10-scan or 100-scan averaging. Limited comparisons with predictions using 60 nm data showed no appreciable difference in predictive capability from the 40 nm data. The best CEC prediction yielded an SEP of 3.59 mEq/100 g for the combination of 0.033 MPa and 1.5 MPa moisture tensions. Moisture content is predicted with an SEP of 1.88 percent water for the dataset including 0.033 MPa, 0.33 MPa, 1.5 MPa, and air dry soil. In terms of the coefficient of variation, the prediction of these two properties is more accurate than the prediction of soil organic carbon. Thus the invention can also find application in the measurement of soil moisture and CEC as well as organic carbon.

Several commercial soil-engaging components were evaluated as mechanisms for preparing a furrow for the reflectance measurement. The chisels and shovels tested did not develop the flat-bottomed furrow required for reflectance sensing. A row unit from a Hiniker Econ-O-Till ridge cleaner did create a flat-bottomed furrow with uniform surface texture and was chosen as the sample presentation mechanism for the in-field tests of the soil sensor.

The selected row unit consists of a horizontal disk row cleaner 100 with attached scraper wings 102 and a leading coulter with depth control bands. The coulter was removed since it would push residue and dry soil into the furrow bottom and possibly corrupt the reflectance measurement. The depth bands 104 were retained to serve as a depth control wheel on the front of the unit. A mounting 108 was fabricated to attach the Hiniker row unit to the three-point hitch of a John Deer 755 compact utility tractor used for the field tests.

The sensor components of FIG. 2 are mounted to the modified Hiniker row cleaner unit described above. The filter disk housing 25 and source 20 are contained in a sealed electrical enclosure 115 attached to the vertical mast 110 of the ridge cleaner unit through vibration isolation mounts 112. The sensor head assembly 65, detector 26, and preamplifier (FIG. 5) are mounted in another sealed electrical enclosure 116, with the quartz window 68 of the sensor head assembly aligned with an aperture in the bottom surface of the enclosure. The fiber optic bundle 24 between these two enclosures is protected inside a length of flexible conduit 118.

The sensor head enclosure 116 is mounted in the light exclusion shield 120, an open-bottomed steel box, which is in turn rigidly attached to the rear of the ridge cleaner row unit. Approximately 20 mm of vertical adjustment in the position of the sensor head relative to the furrow bottom is achieved through mounting slots at the connection between the sensor head enclosure and the light exclusion shield. A rubber skirt 124 extends 10 mm below the lower edge of the light exclusion shield to further protect the sensor from ambient light. The portion of the skirt at the front of the light exclusion shield also serves to smooth the furrow bottom after the passage of the ridge cleaner unit.

Three 12 V deep-cycle batteries are mounted on the tractor to power the sensor and data acquisition system. One battery, mounted on the left fender, provides DC power to the lamp and filter disk-timing circuit. The remaining two batteries, mounted on the front of the tractor, provide power to a 24 V invertor which outputs 115 VAC. The invertor output is conditioned by a regulator and used to power the filter disk motor and the precision power supply for the detector and preamplifier. All sensor components can also be DC powered.

We have found that data acquisition can also be accomplished with the same MetraByte DAS-16 analog and digital I/O board with the DAS-16 installed in an expansion chassis attached to a Zenith Supersport Model 20 laptop computer with an 80C88 processor running at 8 MHz. The computer and expansion chassis are powered by the 115 VAC available on the tractor.

The data acquisition software used is somewhat modified from that used with the 12 MHz AT-Compatible computer. The major functional change required is that the program be able to acquire and store individual data scans. Microsoft QuickBASIC is used to compile the data acquisition program, as it allows all available memory for array storage. This allows at least 450 scans in a 3 min testing run to be stored in an array as they are acquired. The data are written to disk after the run is completed, using a binary format to conserve disk space.

Since this is a slower computer, the data acquisition rate is reduced from the 10 kHz level used in the laboratory to 5 kHz. Tests similar to those described above for determining the sampling rate showed that 5 kHz is a reliable rate with this system.

Hardware triggering is also preferably implemented in the field data acquisition program. A momentary switch mounted within easy reach of the tractor driver is preferably connected to the I/O board digital input port. Once started, the program waits until the switch is closed before beginning data acquisition, allowing the data run to begin at a defined location in the field.

Different hardware and software could be utilized without departing from the invention.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. A soil test apparatus for field use comprising: means adapting said apparatus for transport over a field for testing the soil thereof; infrared radiation generating means for producing infrared radiation at a plurality of predetermined wavelengths; light carrying means coupled to said infrared radiation generating means and extending therefrom for directing infrared radiation onto the soil; and light detecting means for detecting infrared radiation reflected from the soil and for producing corresponding electrical signals.

2. Apparatus according to claim 1 wherein said infrared radiation generating means comprises an infrared source and a circular variable filter monochromator.

3. Apparatus according to claim 1 wherein said infrared radiation generating means comprises an infrared source and a grating monochromator.

4. Apparatus according to claim 1 wherein said infrared radiation generating means comprises an infrared source and a prism monochromator.

5. Apparatus according to claim 1 wherein said light detecting means comprises a single element photodetector.

6. Apparatus according to claim 1 wherein said photodetector comprises a linear array photodetector.

7. Apparatus according to claim 2 wherein said circular variable filter has a wavelength in a range of from substantially 1600 nanometers to substantially 2900 nanometers and a band width of no more than substantially on the order of 60 nanometers.

8. Apparatus according to claim 1 wherein said light carrying means comprises a fiber optic cable.

9. Apparatus according to claim 5 wherein said photodetector comprises a lead sulfide (PbS) near infrared radiation photoelectric detector.

10. Apparatus according to claim 5 wherein said photodetector comprises a lead selenium (PbSe) near infrared radiation photoelectric detector.

11. Apparatus according to claim 5 wherein said photodetector comprises an indium arsenide (InAs) near infrared radiation photoelectric detector.

12. Apparatus according to claim 2 wherein said circular variable filter comprises a quarter-segment circular variable filter having a generally circular disk-like configuration and further including rotating means for rotating said circular variable filter with its center offset from said light source for modulating the infrared radiation from the same by chopping.

13. Apparatus according to claim 12 wherein said means for rotating comprises a servo-controlled motor-generator.

14. Apparatus according to claim 13 wherein said servo-control motor-generator rotates said circular variable filter at a rotational rate of no more than substantially on the order of 600 rpm.

15. Apparatus according to claim 12 and further including rotational sensor means for sensing the rotation rate of said circular variable filter and for producing an electrical signal corresponding to said rate of rotation thereof.

16. Apparatus according to claim 15 wherein said rotational sensor means comprises optointerruptor means for generating a timing pulse corresponding to interruption thereof, and at least one projecting member on said circular variable filter for interrupting said optointerruptor means at least once per revolution of said circular variable filter.

17. Apparatus according to claim 2 wherein said light source comprises a quartz halogen lamp.

18. Apparatus according to claim 2 and further including a spherical biconvex lens mounted intermediate said light source and said circular variable filter for focusing the light from said light source onto said circular variable filter.

19. Apparatus according to claim 12 and further including a light shield having a restricted slit intermediate said light source and said circular variable filter for directing light onto a single controlled area of said circular variable filter as the same rotates relative to said light source in such a manner as to obtain a substantially monochromatic light transmitted by said filter at any given position thereof relative to said slit.

20. Apparatus according to claim 8 wherein said fiber optic cable comprises an elongate fiber optic bundle-type section converter, wherein the fiber area thereof changes from a substantially rectangular cross-section at one end thereof to a substantially circular cross-sectional configuration at the other end thereof.

21. Apparatus according to claim 20 wherein said rectangular cross-sectional end of said fiber optic bundle is mounted to receive light from said circular variable filter and wherein said circular cross-section end thereof is mounted to direct light onto said soil.

22. Apparatus according to claim 1 and further including processing means for receiving said electrical signals from said detector and for determining a predetermined property of said soil therefrom.

23. Apparatus according to claim 22 wherein said electrical signals are AC coupled to said processing means and wherein said processing means includes dynamic baseline correction means for converting said AC coupled signals to a baseline corrected data comprising a DC signal with a baseline level of zero A/D counts.

24. Apparatus according to claim 22 wherein said processing means further includes means for developing a step response curve from a series of said DC signals and further including wavelength calibration means for converting A/D point numbers on said curve to their corresponding wavelengths and for compensating for wavelength variation at least at initial step response portions of said curve, for normalizing the initial portion of the response curve with respect to wavelength.

25. Apparatus according to claim 23 wherein said processing means further includes data point interpolation means for interpolating the baseline corrected data to a standard wavelength spacing.

26. Apparatus according to claim 23 wherein said processor means further includes reflectance calculation means for converting baseline corrected data to decimal reflectance data by comparison against data obtained from a standard ceramic disk reference element with a known reflectance at said predetermined wavelengths.

27. Apparatus according to claim 26 wherein said processing means further includes optical density calculation means for transforming said decimal reflectance data to optical density data.

28. Apparatus according to claim 1 wherein said adapting means comprise means for mounting said apparatus to a vehicle, and further including furrow opening means mounted to said frame means for opening a furrow in the soil as said vehicle transports said apparatus thereover.

29. Apparatus according to claim 28, wherein said infrared radiation generating means is mounted to said frame, said light carrying means extend along said frame for delivering infrared radiation to a furrow opened by said furrow opening means, and said light detecting means is mounted to said frame means adjacent said furrow opening means.

30. A soil test apparatus for field use comprising: frame means for mounting to a vehicle for transporting the apparatus over a field for testing the soil thereof, furrow opening means mounted to said frame means for opening a furrow in the soil as said vehicle transports said apparatus thereover; infrared radiation generating means mounted to said frame for producing infrared radiation at a plurality of predetermined wavelengths; light carrying means coupled to said infrared radiation generating means and extending along said frame for delivering infrared radiation to a furrow opened by said furrow opening means for directing infrared radiation onto the soil; and light detecting means mounted to said frame means adjacent said furrow opening means for detecting infrared radiation reflected from the soil and for producing corresponding electrical signals.

31. A test apparatus for determining constituents of a sample of material comprising: infrared radiation generating means for producing infrared radiation at a plurality of predetermined wavelengths; means for directing light from said infrared radiation generating means onto said sample of material; and light detecting means for detecting infrared radiation reflected from the sample and for producing corresponding electrical signals; wherein said infrared radiation generating means comprises an infrared source and a variable filter; and wherein said variable filter has a wavelength in a range of from substantially 1600 nanometers to substantially 2900 nanometers and a band width of no more than substantially on the order of 60 nanometers.

32. A testing method for determining constituents of a sample of material comprising: producing infrared radiation at a plurality of predetermined wavelengths; directing said infrared radiation onto said sample of material; detecting infrared radiation reflected from the sample, and producing electrical signals corresponding to the detected radiation; wherein the step of producing infrared radiation comprises placing a variable filter in the path of infrared radiation from a fixed source; and wherein said plurality of wavelengths are in a range of from substantially 1600 nanometers to substantially 2900 nanometers and have a band width of no more than substantially on the order of 60 nanometers.

33. Apparatus according to claim 31 wherein said variable filter comprises a circular variable filter monochromator.

34. A method according to claim 32 wherein said variable filter comprises a circular variable filter monochromator.

35. A test apparatus for determining constituents of a sample of material comprising: infrared radiation generating means for producing infrared radiation at a plurality of predetermined wavelengths; means for directing light from said infrared radiation generating means onto said sample of material; and light detecting means for detecting infrared radiation reflected from the sample and for producing corresponding electrical signals; wherein said infrared radiation generating means comprises an infrared source and a variable filter; and further including processing means for receiving said electrical signals from said detector and for determining a predetermined property of said soil therefrom; and wherein said electrical signals are AC coupled to said processing means and wherein said processing means includes dynamic baseline correction means for converting said AC coupled signals to a baseline corrected data comprising a DC signal with a baseline level of zero A/D counts.

36. A testing method for determining constituents of a sample of material comprising: producing infrared radiation at a plurality of predetermined wavelengths; directing said infrared radiation onto said sample of material; detecting infrared radiation reflected from the sample, and producing electrical signals corresponding to the detected radiation; wherein the step of producing infrared radiation comprises placing a variable filter in the path of infrared radiation from a fixed source; and further including the steps of receiving said electrical signals from said detector and determining a predetermined property of said soil therefrom; and wherein said electrical signals are AC coupled prior to said steps of receiving and determining, and further including the step of converting said AC coupled signals to a baseline level of zero A/D counts.

* * * * *